United States Patent [19]

Neubauer et al.

[11] Patent Number: 4,814,511

[45] Date of Patent: Mar. 21, 1989

[54] WORKING UP CYCLOHEXYL HYDROPEROXIDE CONTAINING REACTION MIXTURES

[75] Inventors: Gerald Neubauer, Weinheim; Rolf Schnabel, Schifferstadt; Juergen Hartig, Gruenstadt; Josef Ritz, Ludwigshafen, all of Fed. Rep. of Germany

[73] Assignee: BASF Aktiengesellschaft, Ludwigshafen, Fed. Rep. of Germany

[21] Appl. No.: 111,605

[22] Filed: Oct. 23, 1987

[30] Foreign Application Priority Data

Oct. 23, 1986 [DE] Fed. Rep. of Germany ....... 3636056
Jan. 8, 1987 [DE] Fed. Rep. of Germany ....... 3700336

[51] Int. Cl.$^4$ ............................................. C07C 45/53
[52] U.S. Cl. ................................. 568/342; 568/835; 549/529; 549/530
[58] Field of Search ................ 568/835, 342; 549/529, 549/530

[56] References Cited

U.S. PATENT DOCUMENTS 2,851,496  9/1958  Cates et al. ......................... 568/835
3,912,787  10/1975  Nowack et al. ..................... 568/835

FOREIGN PATENT DOCUMENTS 0092867  11/1983  European Pat. Off. .
0150821  8/1985  European Pat. Off. .
0545758  2/1974  Switzerland .
739051  6/1980  U.S.S.R. .............................. 568/835

OTHER PUBLICATIONS

Kwiatek et al., *J. Am. Chem. Soc.*, vol. 84, pp. 304–305 (1962).
J. Org. Chem. Bd. 45, pp. 4139 to 4143, (1980).

*Primary Examiner*—Bruce D. Gray
*Attorney, Agent, or Firm*—Keil & Weinkauf

[57] ABSTRACT

Cyclohexyl hydroperoxide containing reaction mixtures obtained by oxidation of cyclohexane with molecular oxygen or molecular oxygen containing gases in the liquid phase at from 130° to 200° C. and under from 5 to 125 bar are worked up by reaction with cycloolefins at elevated temperature in the presence of catalysts to react cyclohexyl hydroperoxide with cyclohexene at elevated temperatures in the presence of cyclohexene-soluble compounds of transition metals of groups 4 or 5 or 6 of the periodic table or of one or more cyclohexane-insoluble compounds of a transition metal of group 4 or 5 or 6, or in the presence of selenium, tellurium or a boride, and the resulting cyclohexene oxide at elevated temperatures to cyclohexanol in the presence of hydrogenation catalysts.

7 Claims, No Drawings

WORKING UP CYCLOHEXYL HYDROPEROXIDE CONTAINING REACTION MIXTURES

EP-A-No. 92,867 discloses treating cyclohexyl hydroperoxide containing reaction mixtures from cyclohexane oxidation with aqueous solutions of alkali metal hydroxides, which may contain catalytically active metal salts, to convert the cyclohexyl hydroperoxide present in the reaction mixture to cyclohexanol and cyclohexanone. This process has the disadvantage that it requires substantial amounts of alkali metal hydroxides, which have to be disposed of, and, what is more, considerable amounts of cyclohexanone and/or cyclohexanol are lost through formation of high boilers.

CH Pat. No. 545,758 discloses a process where cyclohexyl hydroperoxide containing reaction mixtures from cyclohexane oxidation are hydrogenatd in the presence of a noble metal catalyst and the resulting hydrogenation mixture is treated with aqueous alkali metal hydroxide solutions. This process likewise has the disadvantage of producing waste liquors which need to be disposed of and substantial amounts of high-boiling by-products. In addition, only one mole of cyclohexanol is obtained per mole of cyclohexyl hydroperoxide.

Use has also been made of supported catalysts for decomposing cyclohexyl hydroperoxide. U.S. Pat. No. 2,851,496 describes metals of group 8 of the periodic table, for example cobalt on activated alumina, as suitable catalysts. However, these catalysts have the disadvantage of being sensitive to water and acid and, for that reason, of having a very short life. In addition, the yield of useful products leaves something to be desired.

SU Pat. No. 739,051 discloses a process where reaction mixturss containing cyclohexyl hydroperoxide are reacted with a cycloolefin such as cyclooctadiene or cyclododecatriene to produce on the one hand cyclohexanol and on the other cyclooctadiene epoxide or cyclododecatriene epoxide. The process has the disadvantage that a mole of cyclohexyl hydroperoxide produces only one mole of cyclohexanol.

Furthermore, it is known from J. org. Chem. 45, 4139–43, that cyclohexene oxide hydrogenates to cyclohexanol. No information is given as to how reaction mixtures containing cyclohexyl hydroperoxide should be treated.

It is an object of the present invention to provide a process for working up a reaction mixture containing cyclohexyl hydroperoxide in which the yield of cyclohexanol is increased, the amount of high-boiling by-products is minimized and no aste liquor in need of treatment is produced.

We have found that this object is achieved with a process for working up a cyclohexyl hydroperoxide cortaining reaction mixture which has been obtained by oxidizing cyclohexane with molecular oxygen or a molecular oxygen containing gas in the liquid phase at from 130° C. to 200° C. and under from 5 to 125 bar by reaction with a cycloolefin at elevated temperatures in the presence of a catalyst, which comprises reacting cyclohexyl hydroperoxide with cyclohexene at elevated temperatures in the presence of a cyclohexane-soluble transition metal compound of group 4 or 5 or 6 of the periodic table or one or more cyclohexane-insoluble compounds of a transition metal of group 4 or 5 or 6, or in the presence of selenium, tellurium or a boride, and then hydrogenating the resulting cyclohexene oxide in a conventional manner in the presence of a hydrogenation catalyst at elevated temperatures to cyclohexanol.

The novel process has the advantage of not producing any waste liquor in need of treatment and of reducing the amount of high-boiling secondary compounds. The process has the further advantage of essentially producing cyclohexanol and in particular of producing up to 2 moles of cyclohexanol per mole of cyclohexyl hydroperoxide and thus of producing a higher amount of useful product per mole of oxidized cyclohexane.

According to the invention, the starting point is a cyclohexyl hydroperoxide containing reaction mixture which has been obtained by oxidizing cyclohexane with molecular oxygen or a molecular oxygen containing gas, for example air, in the liquid phase. The oxidation of cyclohexane is carried out at from 130° to 200° C. under from 5 to 125 bar. Catalysts such as cobalt salts may be present. Advantageously, the oxidation is carried to a conversion of from 2 to 8% by weight, based on starting cyclohexane. Pressure and temperature are adjusted to each other in such a way that the reaction is always in the liquid phase.

In a suitable process, the oxidation of cyclohexane is carried out for example in an upright reaction zone which is subdivided into compartments by perforated plates arranged at regular intervals. The perforated plates advantageously have a free cross-section of from 3 to 20%. Above each perforated plate there are arranged, in even distribution over the cross-section, nozzles having approach orifices which flare into expanded sections whose orifices are pointing downward. Cyclohexane is passed upward through the reaction zone. At the same time gases which contain molecular oxygen, for example in an amount of from 5 to 30% by volume, advantageously air, are introduced through each nozzle orifice to form gas bubbles from 10 to 50 mm in diameter which, in the course of passing upward through the reaction zone, disintegrate into smaller gas bubbles, ie. equilibrium bubbles. The feed rates-for the gas containing the molecular oxygen and for the cyclohexane are adjusted to each other in such a way that the offgas leaving the reaction zone contains not more than 0.1 to 1.5% by volume of molecular oxygen.

In a first stage of a particularly preferred process, molecular oxygen is dissolved in cyclohexane by contacting with molecular oxygen or a molecular oxygen containing gas at from 10° to 50° C. under superatmospheric pressure, for example from 40 to 100 bar, and then, in a second stage, the cyclohexane which contains the dissolved molecular oxygen is passed at from 130° to 250° C. and advantageously under a pressure which is higher by not less than 10 bar through a tubular reaction zone in an approximation of plug flow and without forming a gas phase, the residence time being dimensioned in such a way that it ranges from the time when 50% of the amount of dissolved oxygen has been consumed to 1.2 times the time require for consuming 99.9% of the dissolved oxygen. A suitable process is described for example in EP-A-No. 150,821.

Reaction mixtures of this type can advantageously be enriched before processing by partial distillative removal of cyclohexane, for example by flash distillation in the course of pressure letdown. Typical reaction mixtures contain for example, in addition to cyclohexane, from 0.5 to 5.0% by weight of cyclohexyl hydroperoxide, from 0.1 to 2.5% by weight of cyclohexanol and from 0.1 to 1.5% by weight of cyclohexanone, and also by-products such as esters, carboxylic acids and possibly water in an amount of up to 2% by weight.

Advantageously, such reaction mixtures are washed with water and/or an aqueous alkali metal carbonate solution before further treatment.

In a second stage, cyclohexyl hydroperoxide is expediently reacted, in the reaction mixture in which it has been obtained, with cyclohexene at elevated temperatures in the presence of a cyclohexane-soluble compound of a transition metal of group 4 or 5 or 6 of the periodic table or in the presence of one or more cyclohexane-insoluble compounds of a transition metal of group 4 or 5 or 6, or in the presence of selenium, tellurium or a boride.

Advantageously, from 1 to 5 moles, in particular from 1 to 2 moles, of cyclohexene are added per mole of cyclohexyl hydroperoxide. It is advantageous to use a mixture of cyclohexene and cyclohexane, for example a mixture having cyclohexene content of from 10 to 25% by weight, as obtained by partial hydrogenation of benzene in the presence of a ruthenium catalyst. A suitable process is described for example in U.S. Pat. No. 3,912,787. The reaction is preferably carried out at from 40° to 150° C., in particular at from 60° to 100° C. If the temperature is below the boiling point of cyclohexane it is expedient to employ atmospheric pressure, while at higher temperatures a superatmospheric pressure, for example up to 10 bar, is employed. Pressure and temperature are advantageously adjusted to each other so as to maintain a liquid phase.

The reaction is carried out in the presence of a transition metal compound of group 4 or 5 or 6 of the periodic table which is soluble in cyclohexane, for example a compound of titanium, zirconium, vanadium, niobium, tantalum, chromium, molybdenum or tungsten. Suitable compounds are for example acetylacetonates or salts of higher fatty acids, for example of 8 to 18 carbon atoms, such as 2-ethylhexanoic acid, undecanoic acid, stearic acid or palmitic acid, and also naphthenates. Particular preference is given to compounds of molybdenum, titanium, vanadium and tungsten. Of particular importance are molybdenum compounds. It is advantageous to use from 0.1 to 1.0 millimole of soluble catalyst, calculated as a metal, per mole of cyclohexyl hydroperoxide. The treatment time ranges in general from 20 to 60 minutes.

Other suitable catalysts are cyclohexane-insoluble compounds of metals of groups 4, 5 and 6 of the periodic table, for example titanium, zirconium, vanadium, niobium, tanta-lum, chromium, molybdenum or tungsten. Of particular suitability are oxidic compounds thereof, such as titanium dioxide, zirconium dioxide, vanadium dioxide, chromium oxides, molybdenum oxide, molybdates, tungsten oxide or tungstates.

Other suitable catalysts are cyclohexane-insoluble, preferably oxidic, compounds of selenium or tellurium, such as tellurium dioxide, tellurous acid, selenium dioxide or selenous acid.

Suitable catalysts also include borides such as zinc boride, chromium boride or calcium boride.

These cyclohexane-insoluble catalysts are advantageously employed in amounts of from 0.01 to 5% by weight, based on cyclohexyl hydroperoxide.

Although the catalysts can be used in suspension they are advantageously employed in the fixed form, in particular in the well proven form of a supported catalyst. Suitable carriers for example are active carbon, alumina, silica or silica gel, and also aluminum silicates, in particular zeolites. The amount of active metal compound on the supported catalyst advantageously ranges from 1 to 10% by weight, calculated as catalytically active compound.

The catalytically active metals can also be employed in an ion exchanger bonded form. If the metal is present in the form of a cation, strongly acid ion exchangers, for example crosslinked polystyrene having sulfo groups, are suitable; or if the catalytically active element is present in an acid form, such as selenous acid or a molybdate, it is also possible to use strongly basic ion exchangers, for example crosslinked polystyrene having tertiary or quaternary ammonium groups.

Furthermore, it has proven advantageous to use in addition to the aforementioned catalytically active elements basic compounds from the group of the alkali metal or alkaline earth metal compounds, such as alkali metal carbonates or alkaline earth metal oxides, and also alkali metal-or alkaline earth metal phosphates. Suitable promotors also include aluminum and zinc phosphate.

In a further stage, the cyclohexene oxide formed is hydrogenated at elevated temperatures to cyclohexanol in the presence of a hydrogenation catalyst, expediently in the reaction mixture in which the cyclohexene oxide was produced. Advantageously, the hydrogenation is carried out at from 80° to 150° C., in particular at from 100° to 130° C. The hydrogenation is expediently carried out under a pressure of from 3 to 30 bar, in particular from 10 to 20 bar.

Suitable hydrogenation catalysts are for example metals of subgroup 8 of the periodic table, such as cobalt, nickel, palladium, platinum and ruthenium. The catalysts can be used as such in finely divided form as a suspension or in a fixed form, advantageously deposited on a support such as alumina, coal, magnesium oxide, aluminum silicate or silica. Of proven good utility are palladium catalysts, in particular palladium on active carbon, advantageously in a palladium concentration of from 0.1 to 10% by weight, in particular from 1 to 5% by weight. Another proven system comprises using such a catalyst in a fixed form in a liquid phase or trickle bed process. In the course of the hydrogenation, excess cyclohexene is hydrogenated to cyclohexane, which is separated off with the cyclohexane present as solvent and returned into the oxidation stage. Any unconverted cyclohexyl hydroperoxide still present is hydrogenated to cyclohexanol.

The reaction mixture is distilled to remove cyclohexanol and the cyclohexanone which is likewise present.

The cyclohexanol obtainable by the process of the invention is suitable for preparing adipic acid, an important fiber raw material.

The process of the invention is illustrated by reference to the following examples.

EXAMPLE 1

In a reaction vessel, 300 l of a solution of 85.4 mmol % of cyclohexene, 85.7 mmol % of cyclohexyl hydroperoxide, 36.9 mmol % of cyclohexanol, 18.4 mmol % of cyclohexanone and 0.1 mmol % of MoO2 ethylhexanoate in cyclohexane is heated at 80° C. for 3 hours. Analyzed by gas chromatography, the solution contains after cooling down 19.6 mmol % of cyclohexene, 4.6 mmol % of cyclohexyl hydroperoxide, 107.9 mmol % of cyclohexanol, 26.7 mmol % of cyclohexanone and 65.8 mmol % of cyclohexene oxide.

EXAMPLE 2

Example 1 is repeated using a solution which contains 240.6 mmol % of cyclohexene, 77.5 mmol % of cyclohexyl hydroperoxide, 48.7 mmol % of cyclohexanol and 34 mmol % of cyclohexanone in cyclohexane. The catalyst concentration is 0.1 mmol %. After reaction the solution contains 165.0 mmol % of cyclohexene, 0.8 mmol % of cyclohexyl hydroperoxide, 120.6 mmol % of cyclohexanol, 35.2 mmol % of cyclohexanone and 75.5 mmol % of cyclohexene oxide.

EXAMPLE 3

A reaction tube 90 cm$^2$ in cross-section is packed with 36.5 kg of a 5% strength by weight palladium/active carbon catalyst. The reacted mixture obtained in Example 1 is circulated through this tube at 100° C. under a pressure of 10 bar for 3 hours. The flowrate is 7.5 l/min. At the same time, 450 liters (S.T.P.)/min of hydrogen are passed upward through the reaction tube. The products obtained in vapor form are condensed out of the offgas by cooling and returned into the circulation system. After the reaction has ended, analysis by gas chromatography indicates the presence of 176.4 mmol % of cyclohexanol and of 26.7 mmol % of cyclohexanone. Cyclohexene, cyclohexyl hydroperoxide and cyclohexene oxide are not detectable. The high-boilers content is 0.2% by weight. This corresponds to a loss of 1.0 mmol % of each of cyclohexene oxide and cyclohexanol through etherification of the two compounds.

EXAMPLE 4

(a) Preparation of Catalyst

A strongly acid ion exchanger resin based on styrene/divinylbenzene and having sulfo groups is saturated with a 10% strength by weight aqueous titanium sulfate solution. The ion exchanger loaded with about 5% by weight of titanium is then washed with water, and the remaining acid groups are neutralized with aqueous sodium bicarbonate solution. After renewed washing with water the catalyst is dried.

(b) Reaction of Cyclohexyl Hydroperoxide with Cyclohexene 3 l of a solution of 85.4 mmol % of cyclohexene, 85.7 mmol % of cyclohexyl hydroperoxide, 36.9 mmol % of cyclohexanol and 18.4 mmol % of cyclohexanone in cyclohexane is heated at 80° C. with 360 g of the above-mentioned catalyst for 3 hours. Analysis by gas chromatography indicates a yield of 98% of cyclohexene oxide.

EXAMPLE 5

In a reaction vessel, 3 l of a solution of 85.4 mmol % of cyclohexene, 85 mmol % of cyclohexyl hydroperoxide, 36.9 mmol % of cyclohexanol and 18.4 mmol % of cyclohexanone in cyclohexane are heated with 40 g of cobalt molybdate in suspended form at 80° C. for 3 hours. Analysis by gas chromatography reveals that a yield of 96% of cyclohexene oxide is obtained.

We claim:

1. A process for the recovery of cyclohexanol and cyclohexanone from a cyclohexyl hydroperoxide-containing reaction mixture which has been obtained by oxidizing cyclohexane with molecular oxygen or a molecular oxygen-containing gas in the liquid phase at from 130° to 200° C. and under a pressure of from 5 to 125 bar, comprising the following steps:
    (a) reacting cyclohexyl hydroperoxide with cyclohexene at elevated temperature in the presence of a cyclohexane-soluble compound of a transition metal of group 4 or 5 or 6 of the periodic table or one or more cyclohexane-insoluble compounds of a transition metal of group 4 or 5 or 6 of the periodic table, or in the presence of selenium, tellurium or a boride, to give cyclohexanol and cyclohexene oxide,
    (b) hydrogenating the cyclohexene oxide in the reaction mixture formed in step (a) in the presence of palladium on active carbon at a temperature of from 80° to 150° C. and under a pressure of from 3 to 30 bar, and thereafter
    (c) distilling the reaction mixture to recover cyclohexanol and cyclohexanone.

2. The process of claim 1, wherein from 1 to 5 moles of cyclohexene are used per mole of cyclohexyl hydroperoxide.

3. The process of claim 1, wherein a mixture composed of cyclohexene and cyclohexane and obtained by partial hydrogenation of benzene is used.

4. The process of claim 1, wherein the reaction of cyclohexyl hydroperoxide with cyclohexene is carried out at from 50° to 150° C.

5. The process of claim 1, wherein the catalyst used is a cyclohexane-soluble compound of the metal titanium, vanadium, molybdenum or tungsten or a mixture thereof, or a cyclohexane-insoluble compound of the metal titanium, zirconium, vanadium, niobium, tantalum, chromium, molybdenum or tungsten.

6. The process of claim 1, wherein from 0.0001 to 0.001 mole of a cyclohexane-soluble compound of a transition metal of group 4 or 5 or 6 of the periodic table, calculated as metal, is used per mole of cyclohexyl hydroperoxide.

7. The process of claim 1, wherein the cyclohexane oxidation mixture used has been enriched by partial distillative removal of cyclohexane.

* * * * *